United States Patent [19]

Leuschner et al.

[11] Patent Number: 5,047,012

[45] Date of Patent: Sep. 10, 1991

[54] MOTORIZED SYRINGE WITH MULTIPLE PORT MANIFOLD

[75] Inventors: Ulrich Leuschner, Frankfurt am Main; Felix Ams, Kämpfelbach; Klaus Müller, Knittlingen-Freudenstein, all of Fed. Rep. of Germany

[73] Assignee: Richard Wolf, GmbH, Fed. Rep. of Germany

[21] Appl. No.: 464,019

[22] Filed: Jan. 12, 1990

[30] Foreign Application Priority Data

Feb. 1, 1989 [DE] Fed. Rep. of Germany ....... 3902943

[51] Int. Cl.⁵ .............................................. A61M 1/00
[52] U.S. Cl. ..................................... 604/32; 604/152; 604/224; 417/28; 417/442
[58] Field of Search ..................................... 604/30–32, 604/36, 152, 67, 65, 183, 224; 137/565; 417/28, 442, 461, 462, 502

[56] References Cited

U.S. PATENT DOCUMENTS

| | | | |
|---|---|---|---|
| 1,748,810 | 2/1930 | Wandel | 417/461 X |
| 1,850,273 | 3/1932 | Thayer | 604/7 X |
| 4,218,197 | 8/1980 | Meyer et al. | 417/442 |
| 4,367,736 | 1/1983 | Gupton | 604/30 |
| 4,475,666 | 10/1984 | Bilbrey et al. | 222/14 |
| 4,655,744 | 4/1987 | Thistle et al. | 604/28 |
| 4,662,868 | 5/1987 | Cambio, Jr. | 604/32 |
| 4,723,941 | 2/1988 | Thistle et al. | 604/152 |
| 4,854,324 | 8/1989 | Hirschman et al. | 128/655 |
| 4,902,276 | 2/1990 | Zakko | 604/28 |
| 4,904,237 | 2/1990 | Janese | 604/28 |

FOREIGN PATENT DOCUMENTS 0214629 3/1987 European Pat. Off. .

Primary Examiner—John D. Yasko
Assistant Examiner—Adam J. Cermak
Attorney, Agent, or Firm—Hill, Van Santen, Steadman & Simpson

[57] ABSTRACT

Apparatus for introducing fluids into, and withdrawing fluids from, a hollow organ of the body, in particular a galibladder, for conducting litholysis, comprises a piston-type injection device having a multi-directional valve and which can be removably inserted into an operating mechanism. The injection device has a chamber located in front of its piston and serving as a settling chamber for a mixture of organ secretion and stone sludge removed with the solvent from the hollow organ. The valve is for the sequential connection of the pressure chamber to the hollow organ, to a tank for the solvent, and to a receiving vessel for fluid drawn off.

5 Claims, 1 Drawing Sheet

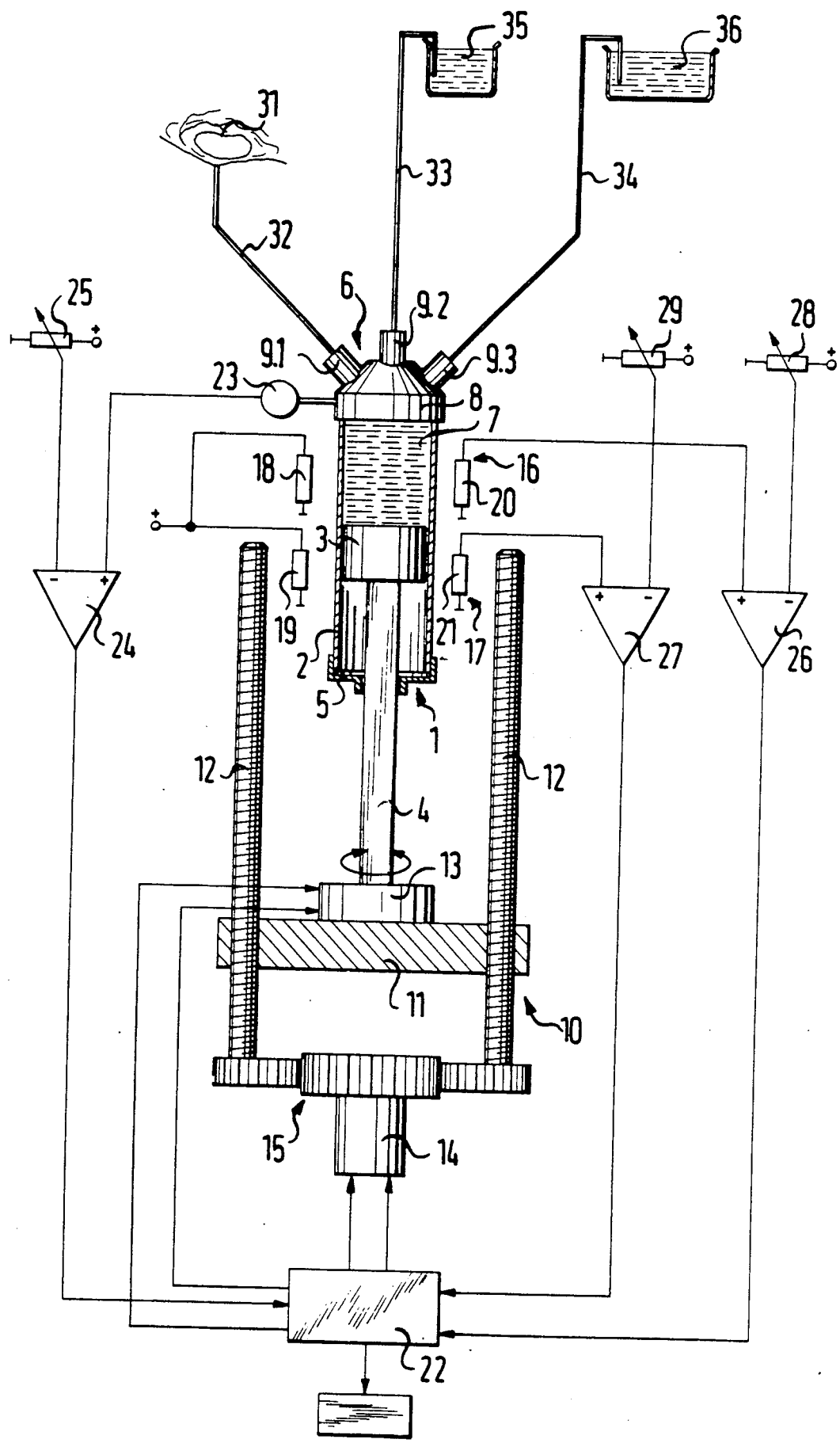

MOTORIZED SYRINGE WITH MULTIPLE PORT MANIFOLD

FIELD OF THE INVENTION

The invention relates to apparatus for introducing a liquid solvent into a hollow organ of the body, in particular the gallbladder, and for drawing off therefrom fluid comprising the solvent, secretion from said organ and sludge arising from dissolution by the solvent, by means of a piston pump, said secretion and the solvent being subsequently separable from one another by means of a trap. The therapy concerned is known as litholysis.

BACKGROUND OF THE INVENTION

European Patent No. 214 629 discloses a device which basically consists of a fluid pump and a trap. In order to break down concretions in the gallbladder, a predetermined quantity of a solvent is introduced into the gallbladder so as to have a dissolving effect upon the concretions. After a specific reaction time, the solvent, together with the secretion from the organ, which has collected in the gallbladder, is drawn off by means of the partial vacuum generated by the fluid pump, into the trap where the secretion, that is to say, the bile, settles in the lower region of the trap since the solvent and the bile can only disperse with respect to one another. The solvent which is then located above the bile can then be reintroduced into the gallbladder to continue the process of dissolving the concretions. The process of supplying and withdrawing the solvent is repeated until either the concretions have been completely dissolved or they have been flushed out as a result of draining the gallbladder. Since, during litholysis, new bile is constantly being produced, it may sometimes be necessary to empty the trap several times in the course of the therapy.

SUMMARY OF THE INVENTION

An object of the invention is to provide a simpler and more user-friendly apparatus for the purpose described above.

In accordance with the invention this object is achieved in that the trap is constituted by the pressure chamber of the piston pump which can be a conventional plunger-type injection device, preferably having a three-way valve.

There is accordingly no need to provide either a separate trap or an additional pump unit comprising a piston and cylinder.

Said plunger-type injection device may have a distribution head having a plurality of connecting channels which are individually connectible to the pressure chamber thereby to afford the possibility of conducting the fluid, drawn from said hollow organ and located in the pressure chamber, into a receiving vessel, simply by changing over channels. By appropriately changing over channels again, fresh solvent can be removed from a storage tank to recharge the plunger-type injection device and solvent supplied to the hollow organ for a fresh cycle of operation of the apparatus. During this procedure the plunger-type injection device does not have to be dismantled.

The apparatus can readily be automated by removably inserting the plunger-type injection device, with its axis vertically aligned and with the distribution head pointing upwards, into an electromotively movable operating mechanism, the operating cycles described above being correspondingly controllable in that the relative torsion between the distribution head and a tube element of said pressure chamber is effected by electromotive torsion of the piston rod of said injection device. Sensors may be provided for monitoring the rate of admission into said pressure chamber, the maximum permissible level of organ secretion therein and the pressure at which solvent is supplied into the gallbladder. The sensors may be light sensitive devices. For overall control of the apparatus, a control logic means may be provided for the control of driving mechanisms for displacing and rotating the piston or piston rod of said injection device in dependence upon control signals and adjustable time bases as well as the entire operating sequence.

BRIEF DESCRIPTION OF THE DRAWING

The single FIGURE is a diagram of an apparatus for introducing a solvent into, and drawing off fluids from, hollow organs of the body.

DETAILED DESCRIPTION OF THE INVENTION

The apparatus comprises a plunger-type injection device 1 having a central, transparent cylindrical tube element 2, preferably made of glass, in which a piston 3 having a piston rod 4 is guided so as to slide tightly. The device 1 also comprises a guide flange 5 which seals off the tube element 2 at its proximal, lower end and guides the piston rod 4 in torsion-free fashion, and a connector 6 which closes the tube element 2 at its distal, upper end, and defines pressure chamber 7 in cooperation with the front end face of the piston 3 and the tube element 2. The connector 6 is in the form of a distribution head 8 having three connecting channels 9.1, 9.2 and 9.3 and is sealingly and rotatably connected to the tube element 2.

The plunger-type injection device 1 is removably inserted, so as to extend vertically, into an operating mechanism 10 which comprises a rack (not shown), the distribution head 8 being fixed in a stationary seat and being uppermost and the free end of the piston rod 4 being connected to a connecting link 11 guided on two screw threaded rotary spindles 12.

The piston rod 4 is coupled to a drive motor 13 for driving it in rotation about its axis. The threaded spindles 12 can be set in rotation synchronously by means of a drive motor 14 by way of a toothed gear 15.

In the region of the pressure chamber 7 are two optical sensors 16 and 17, disposed in spaced apart relationship and at a specific distance from the front face of the piston 3. The sensors 16 and 17 are longitudinally displaceable so that the transparent tube element 2 lies between light transmitters 18 and 19 and their respective light receivers 20 and 21 and is penetrated by the light beams emitted by the transmitters 18 and 19. The sensor 20, whose output is connected to one input of a comparator 26 whose other input is connected to a controller 28, is a first sensor for monitoring the maximum permissible rate of admission of fluid into the pressure chamber.

The apparatus further includes a control logic device comprising a motor control unit 22, a control loop for monitoring a pressure sensor 23 and comprising a comparator 24 and a controller 25, and respective control loops for monitoring the optical sensors 16 and 17 and comprising comparators 26 and 27 and respective controllers 28 and 29.

In order to operate the apparatus, a tube 32 connected to the channel 9.1 of the distribution head 8 is introduced into a hollow bodily organ to be treated, in this case, for example, a gallbladder 31, and the connecting channels 9.2 and 9.3 are respectively connected by means of tubes 33 and 34 to a storage tank 35 for a concretion-dissolving solvent, for example, dimethyl ether, and to a receiving vessel 36 for the resultant mixture of organ secretion, solvent and stone sludge. By actuating the drive motor 14, the piston 3 can then be moved into its upper end position, with the angular position of the piston rod 4 and thus that of the tube element 2, so selected that the connecting channel 9.2 is connected to the pressure chamber 7 so that air can escape from the chamber 7 through the tube 33. Then, by changing the direction of rotation of the drive motor 14, the piston 3 can be withdrawn so that solvent is drawn from the storage tank 35 through the tube 33 into the pressure chamber 7.

In order to initiate the first rinsing cycle, according to the operational program, a connection is established, by actuating the drive motor 13, between the pressure chamber 7 and the connecting channel 9.1 which communicates by way of the tube 32 with the gallbladder 31 to be treated. This switchover is effected because the torque of the drive motor 13 acting on the piston rod 4 of the piston 3 is, as a result of piston rod 4 being, for example, of square cross-section, transmitted to the guide flange 5 which is connected to the tube element 2 so that the tube element 2, which is rotatable relative to the distribution head 8, is rotated relative thereto. The drive motor 14 is then actuated in a direction of rotation to advance the piston 3 to introduce the solvent into the gallbladder 31.

After the solvent has been allowed to react in the gallbladder 31 for a predetermined time, the piston 3 is withdrawn once more, whereupon the partial vacuum so produced in the pressure chamber 7 causes the gallbladder 31 to be emptied. In so doing, the solvent previously introduced into the gallbladder passes with any bile produced in the meantime, and the stone sludge, into the pressure chamber 7. These fluids form a dispersion which separates out after a specific period of rest. The piston 3 is therefore held in its withdrawn position for an appropriate preset settling period in order to allow the individual constituents of the said fluids to settle according to their densities. During this process, the solvent, which has the lowest density, remains at the top of the pressure chamber 7 so that during the next cycle of operation of the apparatus basically only solvent, and at most with small quantities of bile therein, passes back into the gallbladder 31.

The fact that the total quantity of fluid increases from one rinsing cycle to the next because of the constant production of new bile and the greater occurrence of stone sludge is taken into account when drawing the fluid from the gallbladder into the pressure chamber 7, in that the stroke of the piston 3 which is linear, is increased in line with the number of cycles completed. The cycle as described above is repeated until the concretions are dissolved or the residual concretions have been rinsed out by virtue of the alternating action of the flow direction and pressure phases.

Since the solvent becomes enriched with bile and stone sludge from cycle to cycle, the volume percent of the bile and stone sludge accumulating during treatment in the pressure chamber 7 of the plunger-type injection device 1 is monitored by means of the optical sensor 17 which is the second sensor. This produces a signal which is supplied to a first inlet of the comparator 27 as an actual value representing the current volume percent of said bile and stone sludge. A maximum value which represents the maximum admissible volume percent of bile and stone sludge and can be preset by means of the controller 29, is supplied to a second inlet of the comparator 27 to cause it to produce an output signal.

The output signal of the comparator 27 actuates the motor control unit 22 when said actual value equals said maximum value, so that first the sequence of the cycle is interrupted and the drive motor 13 is actuated so that a connection is established between the pressure chamber 7 and the receiving vessel 36 by way of the connecting channel 9.3 and the tube 34. The piston 3 is then advanced again, causing the content of the plunger-type injection device 1 to pass into the receiving vessel 36. By reactuating the driving motor 13, a connection is established between the pressure chamber 7 and the storage tank 35 and, following the procedure outlined above, new solvent is taken up for continuing the treatment.

In the course of the fluid exchange processes described above the tube 32 may become blocked with stone sludge or concretion particles. The resultant increases in pressure or the partial vacuum in the chamber 7 are registered by the pressure sensor 23 whose maximum pressure is adjustable by means of the controller 25. When the actual value measured by the sensor 23 reaches a preset response value of the comparator 24, the latter produces an output signal which brings about the immediate disconnection of the driving motor 14 in order to prevent possible injury to the patient and initiates a visible and/or audible warning signal.

What is claimed is:

1. An apparatus for dissolving concretions in a hollow organ of a body, said apparatus comprising means for introducing liquid solvent into a hollow organ, for withdrawing from the organ a fluid comprising the solvent, secretions from said organ and a sludge formed by the dissolving of a concretion by the solvent, for separating the solvent from the secretions and sludge, and for reintroducing a separate solvent back into the organ, said means including a piston pump having a pressure chamber for introducing said solvent and for drawing off said fluid, said pressure chamber forming a trap for accomplishing a gravitational separation of the secretion and sludge from the solvent, said piston pump including an elongated, cylindrical tube element receiving a piston and being mounted in a vertical direction, means for closing an upper end of the tube element, said means for closing cooperating with the piston to define the pressure chamber and having a distribution head having a plurality of connecting channels individually connecting said pressure chamber to selected lines, a first drive means for moving the piston along an axis of said tube element, sensor means for monitoring the maximum permissible level of said secretions in said chamber and for monitoring the flow pressure of the solvent as it is being introduced into said hollow organ, and control logic means being connected to operate the first drive means in accordance to a sequence program wherein fluid is introduced into the hollow organ, then after a predetermined time the piston is actuated to withdraw the fluid from the organ back into the tube element where it is held to enable separation of the solvent from the other portions of the fluid due to a gravitational separation, and then actuating said piston to reintroduce the solvent back into the hollow organ, said control logic means receiving signals emitted by the sensor means to stop the drive means in response to the flow pressure exceeding a predetermined value and to stop introduction of a solvent once the maximum permissible level of secretions is detected in said chamber.

2. An apparatus according to claim 1 wherein the distribution head has three lines with a first line extending to a container for said solution, a second line extending to a container for waste discharge and third line extending to said hollow organ, said apparatus including means for actuating said distributor head to separately connect each of the three lines to said pressure chamber and said control logic means being connected to said means for actuating to switch the distributor from a position connecting the pressure chamber to the third line to a position connecting it to the second line in response to said sensor means indicating reaching the maximum permissible level so that the fluid in the pressure chamber is discharged to a waste container.

3. An apparatus according to claim 2 wherein the tube element is a transparent element and said sensor means include at least one optical sensor for determining the maximum permissible level of said secretions in said chamber.

4. An apparatus according to claim 2 wherein the sequence program of the logic circuit means increases the stroke of the piston to increase the volume of fluid withdrawn from the organ on each successive step to compensate for the additional secretions of said organ.

5. An apparatus according to claim 1 wherein said sensor means include at least one optical sensor.

* * * * *